United States Patent [19]

Power et al.

[11] Patent Number: 5,756,786
[45] Date of Patent: May 26, 1998

[54] HIGH PURITY TRIMETHYLINDIUM, METHOD OF SYNTHESIS

[75] Inventors: Michael B. Power, Peabody; Deodatta V. Shenai-Khatkhate, Beverly, both of Mass.

[73] Assignee: Morton International, Inc., Chicago, Ill.

[21] Appl. No.: 899,323

[22] Filed: Jul. 23, 1997

Related U.S. Application Data

[63] Continuation-in-part of Ser. No. 881,907, Jun. 25, 1997.
[51] Int. Cl.$^6$ .................................................. C07F 5/00
[52] U.S. Cl. .......................................................... 556/1
[58] Field of Search ................................................ 556/1

[56] References Cited

U.S. PATENT DOCUMENTS 4,847,399  7/1989  Hallock et al. .............................. 556/1

OTHER PUBLICATIONS

Journal of American Chemical Society, "Organometallic Compounds of Group III. I. The Preparation of Gallium and Indium Alkyls from Organoaluminum Compounds".E.
Journal of Crystal Growth 93. Me3 In Preparation and Zone Refining of Adducts for High Quality InP and GaInAs MOVPE.

*Primary Examiner*—Porfirio Nazario-Gonzalez
*Attorney, Agent, or Firm*—Wayne E. Nacker; Gerald K. White

[57] ABSTRACT

Trimethylindium with substantially no oxygen-containing impurities, either as byproduct or associated solvent, is synthesized according to the reaction:

$$Me_zInX_{(3-z)} + (1-1.2)(3-z)Me_3Al + (1-1.2)(6-2z)MF \rightarrow Me_3In + (1-1.2)(3-z)M(Me_2AlF_2) + (1-1.2)(3-z)MX$$

where the Xs are the same or different and are selected from the group consisting of Cl, Br, and I; M is selected from the group consisting of Na, K, Rb, and Cs; and z is 0, 1 or 2 in a hydrocarbon solvent, such as squalane.

18 Claims, No Drawings

HIGH PURITY TRIMETHYLINDIUM, METHOD OF SYNTHESIS

This is a continuation-in-part of copending application Ser. No. 08/881,907, filed on Jun. 25, 1997, (entitled "High Purity Trimethylindium, Method of Synthesis," by inventor Michael B. Power).

The present invention is directed to a method of producing trimethylindium of high purity and to high purity trimethylindium produced by the method.

BACKGROUND OF THE INVENTION

Trimethylindium is a preferred indium source for forming films, such as InP films, in the semiconductor and related electronic industries. As such, trimethylindium must be highly purified, e.g., to be substantially free of detectable levels of metallic impurities such as Sn, Si, Ge, and Zn. A method of producing highly purified indium is described, for example, in U.S. Pat. No. 4,847,399, the teachings of which are incorporated herein by reference. While the method taught in U.S. Pat. No. 4,847,399 provides trimethylindium, as per equations (1) and (2), which is very low in metallic impurities. Using the method of producing trimethylindium described therein, i.e.:

$$InCl_3 + 4MeLi \xrightarrow{(ether)} Me_4InLiOEt_2 \xrightarrow{(heat)} Me_4InLi \quad (1)$$

$$3Me_4InLi + InCl_3 \xrightarrow{(benzene)} 4Me_3In + 3LiCl, \quad (2)$$

trace amounts of the ether invariably remain associated with the trimethylindium, contributing oxygen as an undesirable impurity. Ether is also used in another reaction sequence, as shown in equation (3), for producing trimethylindium in which indium chloride is reacted with methylmagnesium-bromide producing trimethylindium associated with ether and subsequently heating the product to drive off the ether; again trace levels of ether remain associated with the trimethyl indium.

$$InCl_3 + 3MeMgBr \rightarrow InMe_3 + BMgBrCl \quad (3)$$

Furthermore, when trimethylindium is synthesized in the presence of ether, $Me_3In(OEt_2)$ is formed. When trimethylindium is synthesized in the presence of trace oxygen, peroxide and methoxide indium species, $(Me_2InOOMe)_2$ and $(Me_2InOMe)_2$, are formed. Trimethylindium specimens have been reported having low levels of oxygen present in the form of methoxy indium species, although low oxygen levels in the form of etherate i.e. $Me_3InOEt_2$ has not been included in these reports.

An important utility of trimethylindium, and the primary utility to which the highly purified trimethylindium of the present invention is directed, is the use of chemical vapor deposition to produce indium-containing films, such as InP, InAlP, and AlInGaP films. These films are synthesized for opto-electronic applications, such as light-emitting diodes (LEDs). Oxygen, if present in any of the metal sources, such as trimethylindium, becomes incorporated into the crystal growth where it contributes excess electrons which, for example, reduce intensity of light produced by LEDs. Accordingly, trimethylindium of exceedingly high purity, including not only 5-nines purity in respect to metallic impurities, but extremely low oxygen content, are desired.

The present invention synthesizes trimethylindium by a method that produces trimethylindium containing about 50 ppm (parts per million by weight) or less oxygen, including indium peroxides and oxides, and eliminates the possibility of oxygen contained as coordinated ether as well. 50 ppm is the lower limit of detection by fourier transform NMR.

SUMMARY OF THE INVENTION

In accordance with the invention, trimethylindium is synthesized by the reaction

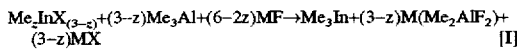

$$Me_zInX_{(3-z)} + (3-z)Me_3Al + (6-2z)MF \rightarrow Me_3In + (3-z)M(Me_2AlF_2) + (3-z)MX \quad [I]$$

where the Xs are the same or different and are selected from F, Cl, Br or I; M is selected from Na, K, Rb, and Cs; and z is 0, 1 or 2. In the preferred case where the Xs are Cl, M is K; and z is 0, the equation becomes:

$$InCl_3 + 3Me_3Al + 6KF \rightarrow Me_3In + 3K(Me_2AlF_2) + 3KCl \quad [II].$$

This represents at least a two-fold excess of KF relative to the reaction taught in the literature:

$$InCl_3 + 3Me_3Al + 3KF \rightarrow Me_3In + 3K(Me_2AlClF) \quad [PA],$$

G. Laube et al., *J. Crystal Growth* 93 (1988) 45–51; and J. J. Eisch, *J. Am. Chem. Soc.*, 84 (1962) 3605. Further in accordance with the invention, the synthesis is carried out in a hydrocarbon (having only hydrogen and carbon atoms) organic solvent having a boiling point of at least 250° C., preferably at least 300° C., and most preferably at least about 325° C., e.g., squalane ($C_{30}H_{64}$).

DETAILED DESCRIPTION OF CERTAIN PREFERRED EMBODIMENTS

Herein, for ease of discussion, the invention will be discussed primarily in terms of reaction (II) where X is Cl; M is K; and z is 0, understanding that the invention can be generalized to include cases where some or all of the Xs are Br or I; where M is Na, Rb or Cs; and where z can be 1 or 2 as per general equation (I).

While Eisch, supra, teaches the synthesis of trialkylindium, in general, it only specifically describes synthesis of triethylindium. Accordingly, it was attempted to follow the specific synthesis of Laube et al., supra, in which the reactants are suspended in pentane, the pentane removed, and the reactants heated to initiate reaction in a solid state. This method proved unsafe, as the exothermic reaction self-initiated prior even to complete removal of the pentane, resulting in a fire. Further adding to the risks of using the Laube et al. procedure is the high reaction temperature described therein which is relatively close to the thermal decomposition temperature of TMI.

In an effort to control the exotherm, the synthesis was repeated, except that the reaction was carried out in a solvent, dodecane, which has a significantly higher boiling point (216° C.) than the pentane described in Laube et al. With the trimethylaluminum (TMA) added dropwise, it proved possible to control the exotherm; however, it was found that despite its relatively higher boiling point, dodecane proved difficult to separate by distillation from the trimethylindium (TMI) product. Organic solvent which is not removed from TMI may produce carbon inclusions in any film which is formed from the TMI and is therefore considered highly undesirable.

Thus, in accordance with a preferred aspect of the invention, synthesis of TMI is conducted in a hydrocarbon that has a boiling point of at least 250° C., more preferably at least 300° C., and even more preferably at least 325° C. An organic solvent particularly suitable is squalane, $C_{30}H_{64}$ (B.P. 350° C., or 176° C. at 0.05 mm Hg). However, other high-boiling solvents, including saturated, unsaturated, straight-chain, branched, cyclic, and aromatic hydrocarbons, are considered suitable. The boiling point of Squalane at atmospheric pressure is 350° C. A list of some other suitable hydrocarbon solvents having a boiling point greater than 250° C. would be for example:

|  | bp | mp |
| --- | --- | --- |
| 1,2-Dimethylnaphthalene | 266.3° C. | –1° C. |
| Squalene | 285/25 mm | –16.9° C. |
| Nonadecane | 330° C. | 32–34° C. |
| Octadecane | 317° C. | 28–30° C. |
| Heptadecane | 302° C. | 22–24° C. |
| Hexadecane | 282–284° C. | 17–19° C. |
| Pentadecane | 270° C. | 9.9° C. |
| Eicosane | 220/30 mm | 36–38° C. |

Thus, the Laube et al. reaction was further carried out in squalane. However, this reaction produced a considerable amount of byproduct, and the TMI product which was isolated did not have the desired purity. It was proposed that the considerable quantity of byproduct indicated that the KF was not completely reacting to form K(Me$_2$AlClF). One possibility proposed was the side reaction:

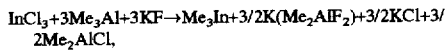
InCl$_3$+3Me$_3$Al+3KF→Me$_3$In+3/2K(Me$_2$AlF$_2$)+3/2KCl+3/ 2Me$_2$AlCl, meaning that the dimethylaluminum chloride reacts with potassium fluoride to form dimethyaluminumfluoride plus potassium chloride, and complex formation between dimethylaluminum chloride and KCl to form K(Me$_2$AlCl$_2$) is not efficient at the temperatures at which the reaction was run.

This problem was solved by employing at least a two-fold excess of potassium fluoride according to reaction (I) above. The excess KF ensures reaction with dimethylaluminumfluoride to form K(Me$_2$AlF$_2$), enabling clean sublimation of TMI product from the crude reaction mixture. Indeed, using KF at at least a two-fold excess produces a much cleaner product from which TMI can be easily isolated by sublimation. Though no less than a two-fold excess is desirable, a slight excess of KF, i.e., up to a 2.2-fold excess may be employed. Above this, no advantages are realized and the additional excess of KF results in additional solid material from which TMI must be separated. Likewise, a slight excess of TMA relative to InCl$_3$, i.e., up to a 0.2 molar excess, may be used to ensure completion of the reaction. Excess TMA will also help to tie up any oxygen-containing species which may be present through whatever vehicle.

Further purification by washing with a non-solvent, e.g., in cyclopentane, and subsequent additional sublimations are useful for removing metallic impurities, such as silicon and germanium species.

By using the method of the present invention, TMI having a total oxygen (from all sources including byproduct and residual solvent) content as measured by Fourier transform NMR of 50 ppm or less, and 5-nines purity (99.999% pure) with respect to metallic impurities is obtained as measured by ICPOES (inductively coupled plasma optical emission spectroscopy).

The method of the invention yields TMI at up to 65–70% of theoretical yield. No ether is involved in the synthesis of the present invention. TMA acts as a scavenger of any oxygen impurities which may be present. Furthermore, the present invention provides process times 2–3 times faster than previous methods.

The invention will now be described in greater detail by way of specific example.

EXAMPLE

To a 12 L. stainless steel kettle head pot equipped with a thermowell, mechanical stirrer, and nitrogen inlet were added 1500 g. KF, 800 g. of InCl$_3$, and then 4 L. squalane. A dropping funnel was attached through which 100 ml. of TMA was added dropwise to the mechanically stirred mixture. White smoke was briefly observed at the addition of the first few milliliters of TMA, but this disappeared quickly. The mixture was stirred for two hours. The remaining TMA (to make 800 g. total) was then added over a 2½ hour period with the pot heated to 125° C. and the content temperature, as measured through a thermowell in the kettle, maintained between 100° and 105° C. After addition of all TMA, the mixture was heated under nitrogen for an additional 3½ hours at between 100° and 120° C., and the contents then cooled to room temperature.

The dropping funnel was removed and replaced with a dry ice cooled condenser hooked up to a dry ice cooled receiver via a U-tube. A vacuum of 0.05 mm Hg was applied. TMI could be seen condensing into the dry ice cooled receiver. The pot was warmed slowly to 58° C. to produce a thermowell temperature of 45° C., and sublimation was carried out for a total of 12 hours with a maximum pot temperature of 70° C., a maximum thermowell temperature of 65° C. The yield of TMI obtained was 375 g. (64.87%). Fourier transform NMR indicated that no peaks representing oxygenated species could be observed. In order to minimize possible contamintion from metallic species, the recovered TMI was washed in cyclopentane and resublimated. 325 grams of final TMI was obtained, representing a yield of ultrapure product around 56.2%. Fourier transform NMR was conducted on the sample. Again, no peaks representing oxygenated species could be observed. ICP analysis indicated "non-detectable" with regard to metallic impurities.

What is claimed is:

1. A method of producing trimethylindium (TMI) comprising conducting the reaction

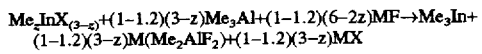
Me$_z$InX$_{(3-z)}$+(1–1.2)(3–z)Me$_3$Al+(1–1.2)(6–2z)MF→Me$_3$In+ (1–1.2)(3–z)M(Me$_2$AlF$_2$)+(1–1.2)(3–z)MX where the Xs are the same or different and are selected from the group consisting of Cl, Br, and I; M is selected from the group consisting of Na, K, Rb, and Cs; and z is 0, 1 or 2 in a hydrocarbon solvent.

2. The method according to claim 1 wherein z is 0.
3. The method according to claim 1 wherein all Xs is Cl.
4. The method according to claim 3 wherein z is 0.
5. The method according to claim 1 where M is K.
6. The method according to claim 5 wherein all Xs is Cl.
7. The method according to claim 6 wherein z is 0.
8. The method according to claim 1 wherein said solvent has a boiling point of at least 250° C.
9. The method according to claim 1 wherein said solvent has a boiling point of at least 300° C.
10. The method according to claim 1 wherein said solvent has a boiling point of at least 325° C.
11. The method according to claim 1 wherein said solvent is selected from the group consisting of squalane, 1,2- dimethylnaphthalene, nonadecane, octadecane, heptadecane, hexadecane, pentadecane, eicosane and mixtures thereof.

12. The method according to claim 1 wherein said solvent is squalane.

13. A method of producing trimethylindium comprising conducting the reaction

$$InX_3 + 3Me_3Al + 6KF \rightarrow Me_3In + 3K(Me_2AlF_2) + 3KX$$

where X is selected from the group consisting of Cl, Br, and I and with the proviso that $Me_3Al$ may be employed in the reaction at up to a 0.2 molar excess relative to $InX_3$, up to 6.6 moles of KF may be employed, and wherein said reaction is conducted with the reactants suspended within a hydrocarbon solvent having a boiling point of at least 250° C.

14. A method according to claim 13 wherein X is Cl.

15. A method according to claim 13 wherein said solvent has a boiling point of at least 300° C.

16. A method according to claim 13 wherein said solvent has a boiling point of at least 325° C.

17. A method according to claim 13 wherein said solvent is selected from the group consisting of squalane, 1,2-dimethylnaphthalene, nonadecane, octadecane, heptadecane, hexadecane, pentadecane, eicosane and mixtures thereof.

18. A method according to claim 13 wherein said solvent is squalane.

* * * * *